(12) United States Patent
Measamer et al.

(10) Patent No.: US 7,918,377 B2
(45) Date of Patent: Apr. 5, 2011

(54) SURGICAL STAPLING INSTRUMENT WITH APPARATUS FOR PROVIDING ANVIL POSITION FEEDBACK

(75) Inventors: John P. Measamer, Cincinnati, OH (US); Frederick E. Shelton, IV, Hillsboro, OH (US); Chester O. Baxter, III, Loveland, OH (US); Richard P. Fuchs, Cincinnati, OH (US); Nicholas G. Molitor, Milford, OH (US); Bennie Thompson, Cincinnati, OH (US); Mark Tsonton, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 286 days.

(21) Appl. No.: 12/252,502

(22) Filed: Oct. 16, 2008

(65) Prior Publication Data

US 2010/0096435 A1    Apr. 22, 2010

(51) Int. Cl.
*A61B 17/068*    (2006.01)
(52) U.S. Cl. .................... 227/180.1; 227/19; 227/175.2; 227/176.1; 606/139; 606/219
(58) Field of Classification Search .................... 227/19, 227/175.2, 176.1, 180.1; 606/139, 153, 219
See application file for complete search history.

(56) References Cited

U.S. PATENT DOCUMENTS

| | | | |
|---|---|---|---|
| 5,104,025 A | | 4/1992 | Main et al. |
| 5,205,459 A | | 4/1993 | Brinkerhoff et al. |
| 5,285,945 A | | 2/1994 | Brinkerhoff et al. |
| 5,309,927 A | | 5/1994 | Welch |
| 5,411,508 A | * | 5/1995 | Bessler et al. ................ 606/153 |
| 5,518,164 A | * | 5/1996 | Hooven ............................ 227/5 |
| 5,667,517 A | * | 9/1997 | Hooven ......................... 606/151 |
| 5,693,042 A | * | 12/1997 | Boiarski et al. ................. 606/10 |
| 6,024,741 A | * | 2/2000 | Williamson et al. ........... 606/40 |
| 6,302,311 B1 | * | 10/2001 | Adams et al. .............. 227/176.1 |
| 6,605,078 B2 | * | 8/2003 | Adams ............................. 606/1 |
| 6,629,630 B2 | * | 10/2003 | Adams ....................... 227/180.1 |
| 6,716,233 B1 | * | 4/2004 | Whitman ..................... 606/219 |
| 6,945,444 B2 | | 9/2005 | Gresham et al. |
| 7,234,624 B2 | * | 6/2007 | Gresham et al. ........... 227/179.1 |
| 7,235,089 B1 | * | 6/2007 | McGuckin, Jr. .............. 606/167 |

(Continued)

FOREIGN PATENT DOCUMENTS

CA    2458946 A1    3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Scott A. Smith

(57) ABSTRACT

Circular stapling instruments for cutting and applying one or more surgical staples to tissue are disclosed. The instruments include various forms of feedback systems designed to provide at least one mode of feedback to the surgeon when the anvil has been attached to the device and/or when the anvil has been attached to the device and oriented in a firing position. Various types of feedback indicators are disclosed such as illumination devices, sound generating devices and vibration generation devices. In various embodiments, the feedback indicator comprises at least one illumination device mounted on the anvil which indicates that the anvil has been properly attached to the instrument and which can also serve to illuminate the surgical site.

19 Claims, 10 Drawing Sheets

U.S. PATENT DOCUMENTS

| | | |
|---|---|---|
| 7,354,447 B2 | 4/2008 | Shelton, IV et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 2006/0278680 A1 | 12/2006 | Viola et al. |
| 2007/0045379 A1 | 3/2007 | Shelton, IV |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0242610 A1 | 10/2009 | Shelton, IV et al. |
| 2009/0289096 A1 | 11/2009 | Shelton, IV et al. |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0133317 A1 | 6/2010 | Shelton, IV et al. |
| 2010/0133318 A1 | 6/2010 | Boudreaux |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |

| | | | | | | |
|---|---|---|---|---|---|---|
| DE | 10314072 | A1 | 10/2004 | EP | 1479346 B1 | 1/2007 |
| EP | 0122046 | A1 | 10/1984 | EP | 1484024 B1 | 1/2007 |
| EP | 0070230 | B1 | 10/1985 | EP | 1754445 A2 | 2/2007 |
| EP | 0033548 | B1 | 5/1986 | EP | 1759812 A1 | 3/2007 |
| EP | 0276104 | A2 | 7/1988 | EP | 1769756 A1 | 4/2007 |
| EP | 0639349 | A2 | 2/1994 | EP | 1769758 A1 | 4/2007 |
| EP | 0324636 | B1 | 3/1994 | EP | 1785097 A2 | 5/2007 |
| EP | 0593920 | A1 | 4/1994 | EP | 1790293 A2 | 5/2007 |
| EP | 0600182 | A2 | 6/1994 | EP | 1800610 A1 | 6/2007 |
| EP | 0630612 | A1 | 12/1994 | EP | 1300117 B1 | 8/2007 |
| EP | 0634144 | A1 | 1/1995 | EP | 1813199 A1 | 8/2007 |
| EP | 0646356 | A2 | 4/1995 | EP | 1813201 A1 | 8/2007 |
| EP | 0646357 | A1 | 4/1995 | EP | 1813203 A2 | 8/2007 |
| EP | 0653189 | A2 | 5/1995 | EP | 1813207 A1 | 8/2007 |
| EP | 0669104 | A1 | 8/1995 | EP | 1813209 A1 | 8/2007 |
| EP | 0511470 | B1 | 10/1995 | EP | 1402821 B1 | 12/2007 |
| EP | 0679367 | A2 | 11/1995 | EP | 1872727 A1 | 1/2008 |
| EP | 0392547 | B1 | 12/1995 | EP | 1839596 A2 | 2/2008 |
| EP | 0685204 | A1 | 12/1995 | EP | 1897502 A1 | 3/2008 |
| EP | 0699418 | A1 | 3/1996 | EP | 1702568 B1 | 7/2008 |
| EP | 0702937 | A1 | 3/1996 | EP | 1970014 A1 | 9/2008 |
| EP | 0705571 | A1 | 4/1996 | EP | 1980213 A2 | 10/2008 |
| EP | 0484677 | B2 | 6/1996 | EP | 1759645 B1 | 11/2008 |
| EP | 0541987 | B1 | 7/1996 | EP | 1693008 B1 | 12/2008 |
| EP | 0667119 | B1 | 7/1996 | EP | 2000102 A2 | 12/2008 |
| EP | 0770355 | A1 | 5/1997 | EP | 1749486 B1 | 3/2009 |
| EP | 0503662 | B1 | 6/1997 | EP | 2090256 A2 | 8/2009 |
| EP | 0578425 | B1 | 9/1997 | EP | 1813206 B1 | 4/2010 |
| EP | 0625335 | B1 | 11/1997 | FR | 999646 A | 2/1952 |
| EP | 0552423 | B1 | 1/1998 | FR | 1112936 A | 3/1956 |
| EP | 0592244 | B1 | 1/1998 | FR | 2765794 A | 1/1999 |
| EP | 0648476 | B1 | 1/1998 | GB | 939929 A | 10/1963 |
| EP | 0676173 | B1 | 9/1998 | GB | 1210522 A | 10/1970 |
| EP | 0603472 | B1 | 11/1998 | GB | 2336214 A | 10/1999 |
| EP | 0605351 | B1 | 11/1998 | JP | 6007357 A | 1/1994 |
| EP | 0878169 | A1 | 11/1998 | JP | 7051273 A | 2/1995 |
| EP | 0879742 | A1 | 11/1998 | JP | 8033641 A | 2/1996 |
| EP | 0760230 | B1 | 2/1999 | JP | 8229050 A | 9/1996 |
| EP | 0537572 | B1 | 6/1999 | JP | 2000287987 A | 10/2000 |
| EP | 0552050 | B1 | 5/2000 | JP | 2001286477 A | 10/2001 |
| EP | 1090592 | A1 | 4/2001 | JP | 2002369820 A | 12/2002 |
| EP | 1256318 | B1 | 5/2001 | JP | 2005505322 T | 2/2005 |
| EP | 0908152 | B1 | 1/2002 | JP | 2005103293 A | 4/2005 |
| EP | 0872213 | B1 | 5/2002 | RU | 2187249 C2 | 8/2002 |
| EP | 1238634 | A2 | 9/2002 | RU | 2225170 C2 | 3/2004 |
| EP | 0656188 | B1 | 1/2003 | SU | 1377053 A1 | 2/1988 |
| EP | 0829235 | B1 | 6/2003 | SU | 1561964 A1 | 5/1990 |
| EP | 0813843 | B1 | 10/2003 | SU | 1722476 A1 | 3/1992 |
| EP | 0741996 | B1 | 2/2004 | WO | WO 93/08755 A1 | 5/1993 |
| EP | 0705570 | B1 | 4/2004 | WO | WO 95/18572 A1 | 7/1995 |
| EP | 1086713 | B1 | 5/2004 | WO | WO 95/23557 A1 | 9/1995 |
| EP | 1426012 | A1 | 6/2004 | WO | WO 95/29639 A1 | 11/1995 |
| EP | 0888749 | B1 | 9/2004 | WO | WO 96/22055 A1 | 7/1996 |
| EP | 1477119 | A1 | 11/2004 | WO | WO 96/35464 A1 | 11/1996 |
| EP | 1479345 | A1 | 11/2004 | WO | WO 97/34533 A1 | 9/1997 |
| EP | 1479347 | A1 | 11/2004 | WO | WO 97/39688 A2 | 10/1997 |
| EP | 1479348 | A1 | 11/2004 | WO | WO 98/17180 A1 | 4/1998 |
| EP | 1520521 | A1 | 4/2005 | WO | WO 98/30153 A1 | 7/1998 |
| EP | 1520523 | A1 | 4/2005 | WO | WO 99/12483 A1 | 3/1999 |
| EP | 1520525 | A1 | 4/2005 | WO | WO 99/15086 A1 | 4/1999 |
| EP | 1522264 | A1 | 4/2005 | WO | WO 99/34744 A1 | 7/1999 |
| EP | 1550408 | A1 | 7/2005 | WO | WO 99/45849 A1 | 9/1999 |
| EP | 1557129 | A1 | 7/2005 | WO | WO 00/24322 A1 | 5/2000 |
| EP | 1064883 | B1 | 8/2005 | WO | WO 00/57796 A1 | 10/2000 |
| EP | 1157666 | B1 | 9/2005 | WO | WO 00/64365 A1 | 11/2000 |
| EP | 1621138 | A2 | 2/2006 | WO | WO 00/72762 A1 | 12/2000 |
| EP | 1621139 | A2 | 2/2006 | WO | WO 00/72765 A1 | 12/2000 |
| EP | 1621141 | A2 | 2/2006 | WO | WO 01/05702 A1 | 1/2001 |
| EP | 1621145 | A2 | 2/2006 | WO | WO 01/10482 A1 | 2/2001 |
| EP | 1621151 | A2 | 2/2006 | WO | WO 01/54594 A1 | 8/2001 |
| EP | 1652481 | A2 | 5/2006 | WO | WO 01/62158 A2 | 8/2001 |
| EP | 1382303 | B1 | 6/2006 | WO | WO 01/62162 A1 | 8/2001 |
| EP | 1045672 | B1 | 8/2006 | WO | WO 01/62164 A2 | 8/2001 |
| EP | 1617768 | B1 | 8/2006 | WO | WO 01/91646 A1 | 12/2001 |
| EP | 1702567 | A2 | 9/2006 | WO | WO 02/07608 A2 | 1/2002 |
| EP | 1129665 | B1 | 11/2006 | WO | WO 02/07618 A1 | 1/2002 |
| EP | 1256317 | B1 | 12/2006 | WO | WO 02/17799 A1 | 3/2002 |
| EP | 1728473 | A1 | 12/2006 | WO | WO 02/19920 A1 | 3/2002 |
| EP | 1728475 | A2 | 12/2006 | WO | WO 02/30297 A2 | 4/2002 |

| | | | |
|---|---|---|---|
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/ abstract?CRETRY=1&SRETRY=0; [online] accessed: Sep. 22, 2008 (2 pages).

International Search Report for PCT/US2009/060965, dated Feb. 8, 2010 (6 pages).

The Sodem Aseptic Battery Transfer Kit, Sodem Systems, 2000, 3 pages.

* cited by examiner

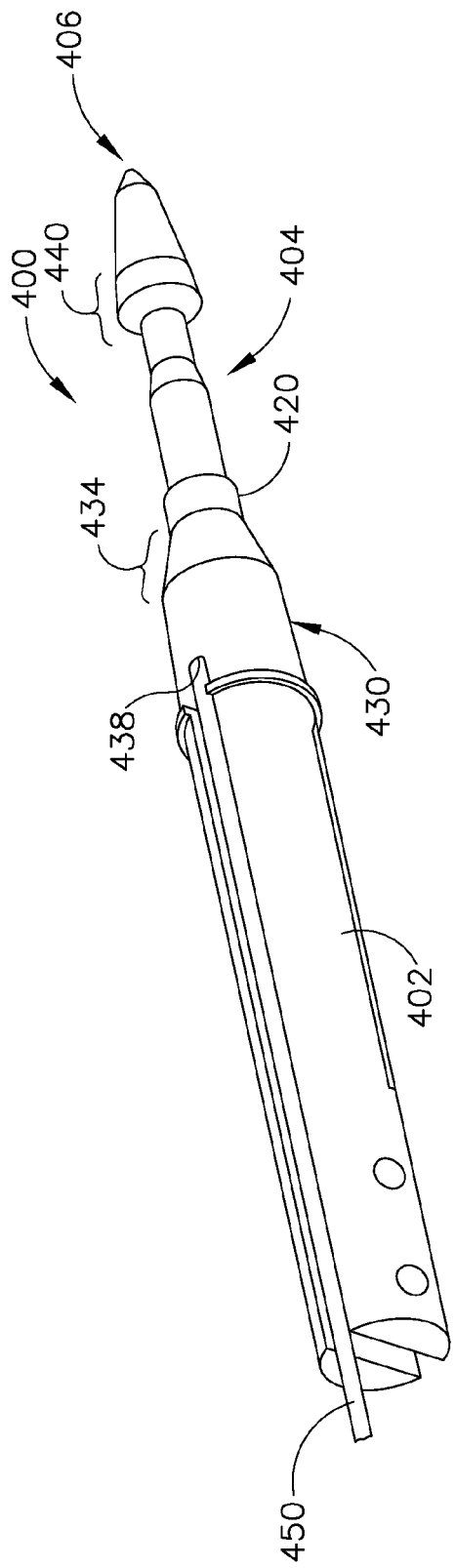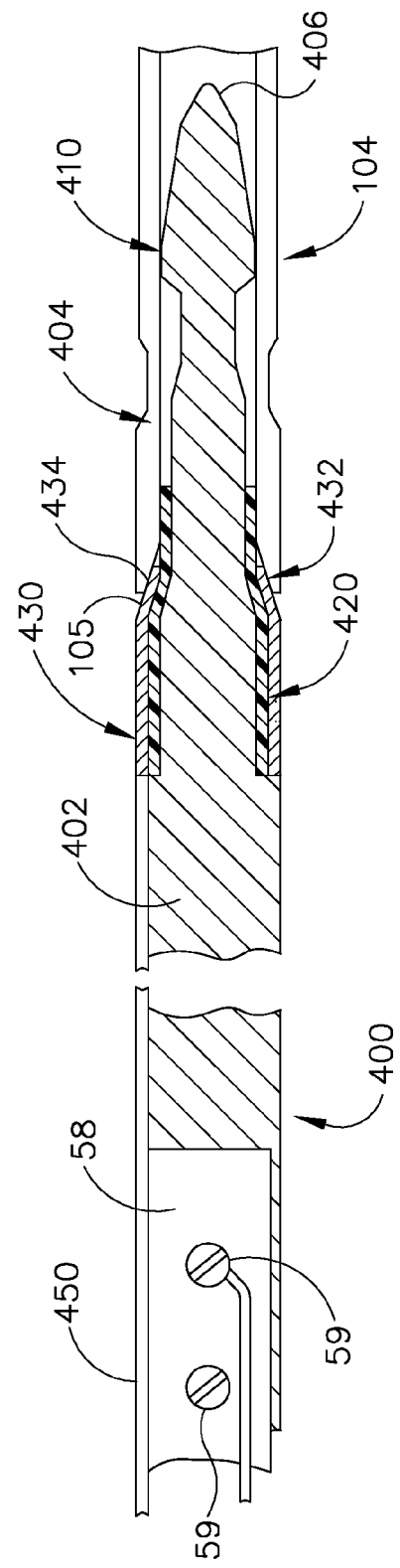
FIG. 10
FIG. 11

SURGICAL STAPLING INSTRUMENT WITH APPARATUS FOR PROVIDING ANVIL POSITION FEEDBACK

FIELD OF THE INVENTION

The present invention generally relates to surgical staplers, and more particularly, to circular stapling instruments for performing anastomosis stapling operations.

BACKGROUND

In certain types of surgical procedures, the use of surgical staples has become the preferred method of joining tissue and, as such, specially configured surgical staplers have been developed for these applications. For example, intra-luminal or circular staplers have been developed for use in a surgical procedure known as an anastomosis. Circular staplers useful for performing an anastomosis are disclosed, for example, in U.S. Pat. Nos. 5,104,025; 5,205,459; 5,285,945; and 5,309,927 which are each herein incorporated by reference in their respective entireties.

One form of an anastomosis comprises a surgical procedure wherein sections of intestine are joined together after a diseased portion has been excised. The procedure requires re-joining the ends of the two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular staplers has greatly simplified the anastomosis procedure and also decreased the time required to perform an anastomosis.

In general, a conventional circular stapler typically consists of an elongated shaft that has a proximal actuating mechanism and a distal stapling mechanism mounted to the shaft. The distal stapling mechanism commonly consists of a fixed stapling cartridge that contains a plurality of staples configured in a concentric circular array. A round cutting knife is concentrically mounted in the cartridge interior to the staples for axial travel therein. Extending axially from the center of the cartridge is a movable trocar shaft that is adapted to have a staple anvil removably coupled thereto. The anvil is configured to form the ends of the staples as they are driven into it. The distance between a distal face of the staple cartridge and the staple anvil is controlled by an adjustment mechanism mounted to the proximal end of the stapler shaft for controlling the axial movement of the trocar. Tissue clamped between the staple cartridge and the staple anvil is simultaneously stapled and cut when the actuating mechanism is activated by the surgeon.

When performing an anastomosis using a circular stapler, the intestine is typically stapled using a conventional surgical stapler with double rows of staples being emplaced on either side of the diseased portion of intestine to be removed. The target section is simultaneously cut as the adjoining end is stapled. After removing the diseased portion, the surgeon typically inserts the anvil into the proximal end of the lumen, proximal of the staple line. This is done by inserting the anvil head into an entry port cut into the proximal lumen by the surgeon. On occasion, the anvil can be placed transanally, by placing the anvil head on the distal end of the stapler and inserting the instrument through the rectum. The surgeon then ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby clamping the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, the concentric circular knife blade is driven through the intestinal tissue ends, cutting the ends adjacent to the inner row of staples. The surgeon then withdraws the stapler from the intestine and the anastomosis is complete.

During the aforementioned stapling process, it is often difficult for the surgeon to effectively view the area of the colon being cut and stapled. To assist the surgeon, separate endoscopes equipped with cameras and lighting systems are employed. However, due to the limited amount of space available to maneuver and position such instrument within the colon, such instruments may not supply a desired amount of illumination to the area. Thus, there is a need for a circular stapler that is equipped with a source of illumination.

During the above-described surgical procedures, the need exists to provide feedback to the surgeon that the anvil is properly attached to the device prior to closing and firing. For example, in a lower anterior resection, it is often difficult for the surgeon to know if they have successfully attached the anvil to the trocar. Adverse outcomes may occur if the stapler is fired prior to securing the anvil to the device. Thus another need exists for a device for indicating when the anvil has been properly attached to the device.

Also during the above-described surgical procedures, it is often difficult for the surgeon to know when the anvil has been moved to the desired closed position wherein it is ready to be fired. Thus, there is a need for a feedback arrangement for a circular stapler that provides the surgeon with an indication that the anvil has been moved to the desired firing position.

The foregoing discussion is intended only to illustrate some of the shortcomings present in the field of the invention at the time, and should not be taken as a disavowal of claim scope.

BRIEF SUMMARY

The invention overcomes the above-noted and other deficiencies of the prior art by providing a surgical stapling instrument for applying one or more surgical staples to tissue. Various embodiments comprise a handle assembly and a shaft assembly that is coupled to the handle assembly and which movably supports a trocar assembly therein. The surgical stapling instrument may further comprise a stapling head assembly that is operably coupled to the shaft assembly. The stapling head assembly may comprise a staple cartridge for supporting one or more surgical staples and a staple driver assembly for engaging and driving the staples from the staple cartridge. A knife may be movably supported in the stapling head assembly. A drive system may be provided to apply drive motions to the staple driver assembly. An anvil may be removably attachable to a distal end of the trocar assembly and an indicator system may operably communicate with the trocar assembly for providing an indication signal when the anvil is attached to the distal end of the trocar assembly.

In another general aspect of the present invention, there is provided a surgical stapling instrument for applying one or more surgical staples to tissue. Various embodiments may comprise a handle assembly and a shaft assembly that is coupled to the handle assembly and movably supports a trocar assembly therein. A stapling head assembly is operably coupled to the shaft assembly. The stapling head assembly may comprise a staple cartridge for supporting one or more surgical staples and a staple driver for engaging and driving the staples from the staple cartridge. A knife may also be movably supported in the stapling head assembly. The surgical stapling instrument may further include a drive system for applying drive motions to the staple driver assembly and the knife. An anvil may be removably attachable to a distal end of the trocar assembly. An illumination device may be attached to the anvil. The illumination device may be electrically connected to a source of electrical current. A sensor may be provided on one of the anvil and the trocar assembly and be electrically coupled to the source of electrical current and the illumination device such that when the anvil is attached to the distal end portion of the trocar assembly, electrical current flows from the source of electrical current to the illumination device.

In accordance with another general form of the present invention, there is provided a surgical stapling instrument for applying one or more surgical staples to tissue. Various embodiments comprise a handle assembly and a shaft assembly that is coupled to the handle assembly. A stapling head assembly may be operably coupled to the shaft assembly. The stapling head assembly may comprise a staple cartridge for supporting one or more surgical staples, a staple driver for engaging and driving the staples from the staple cartridge. A knife may be movably supported in the stapling head assembly. A drive system may be provided for applying drive motions to the staple driver and the knife. The instrument may further include a source of electrical current. An indicator may also be provided on the instrument. The indicator may communicate with the source of electrical current. A trocar assembly may be movably supported by the shaft assembly and be configured to detachably support an anvil thereon. The trocar assembly may have a plurality of contact regions that communicate with the source of electrical current and the indicator. At least some of the contact regions may be electrically insulated from the first contact region such that when the anvil is attached to the distal end of the trocar assembly, the anvil electrically connects the first and second contact regions to permit the electrical current to flow to the indicator.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 is perspective view of a portion of a trocar of an embodiment of the present invention;

FIG. 11 is a partial cross-sectional view of a portion of an anvil received on a distal end portion of the trocar of FIG. 10;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Turning to the Drawings, wherein like numerals denote like components, there is shown a circular stapler 10 that includes a unique and novel system for providing feedback to the surgeon to indicate when the detachable anvil 100 thereof has been properly attached to the stapler 10. A variety of different circular staplers are known in the art. FIGS. 1-8 illustrate an exemplary circular stapler arrangement that may employ the benefits of various aspects of the present invention. It is conceivable, however, that the various embodiments of the present invention may be successfully employed with other stapler constructions without departing from the spirit and scope of the present invention.

It will be appreciated that the terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up" and "down" may be used herein with respect to the drawings. However, surgical instruments are used in many orientations and positions, and these terms are not intended to be limiting and/or absolute.

Figure 1:
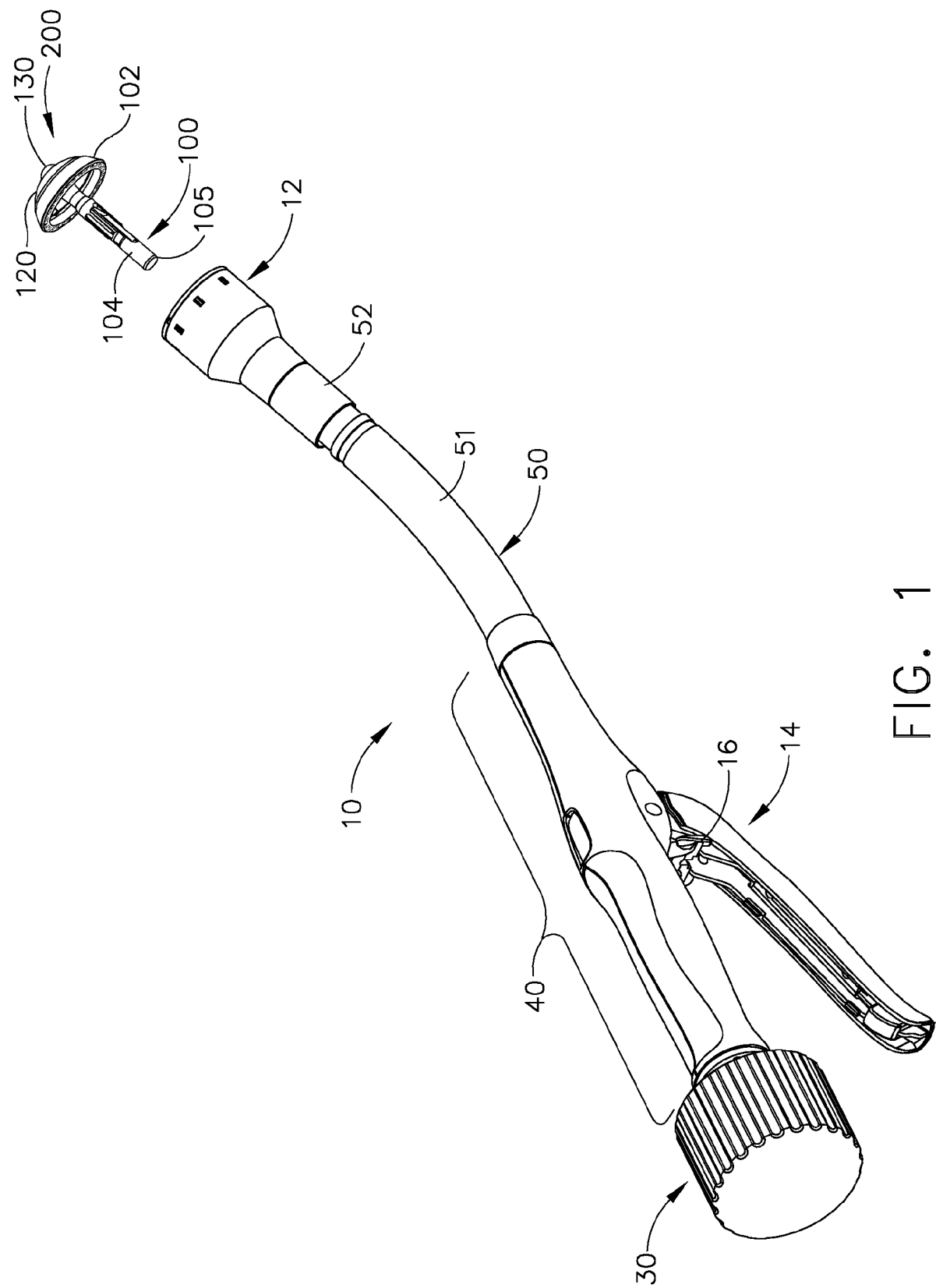
FIG. 1 is a perspective view of a surgical stapler that may be employed in connection with various embodiments of the present invention.

As can be seen in FIG. 1, there is disclosed a circular stapler 10 that includes a stapling head assembly 12, an anvil 100, an adjustment knob 30, and a trigger 14. The stapling head assembly 12 is coupled to a handle assembly 40 by a shaft assembly 50. The trigger 14 is pivotally supported by the handle assembly 40 and is configured to operate the stapler 10 when a safety mechanism 16 is released. When the trigger 14 is activated, a drive system operates within the shaft assembly 50 so that staples 90 (FIG. 2) are expelled from the stapling head assembly 12 into forming contact with the anvil 100. Simultaneously, a knife 70, that is operably supported within the head 12, acts to cut tissue held within the circumference of the stapled tissue. The stapler 10 is then pulled through the tissue leaving stapled tissue in its place.

Figure 2:
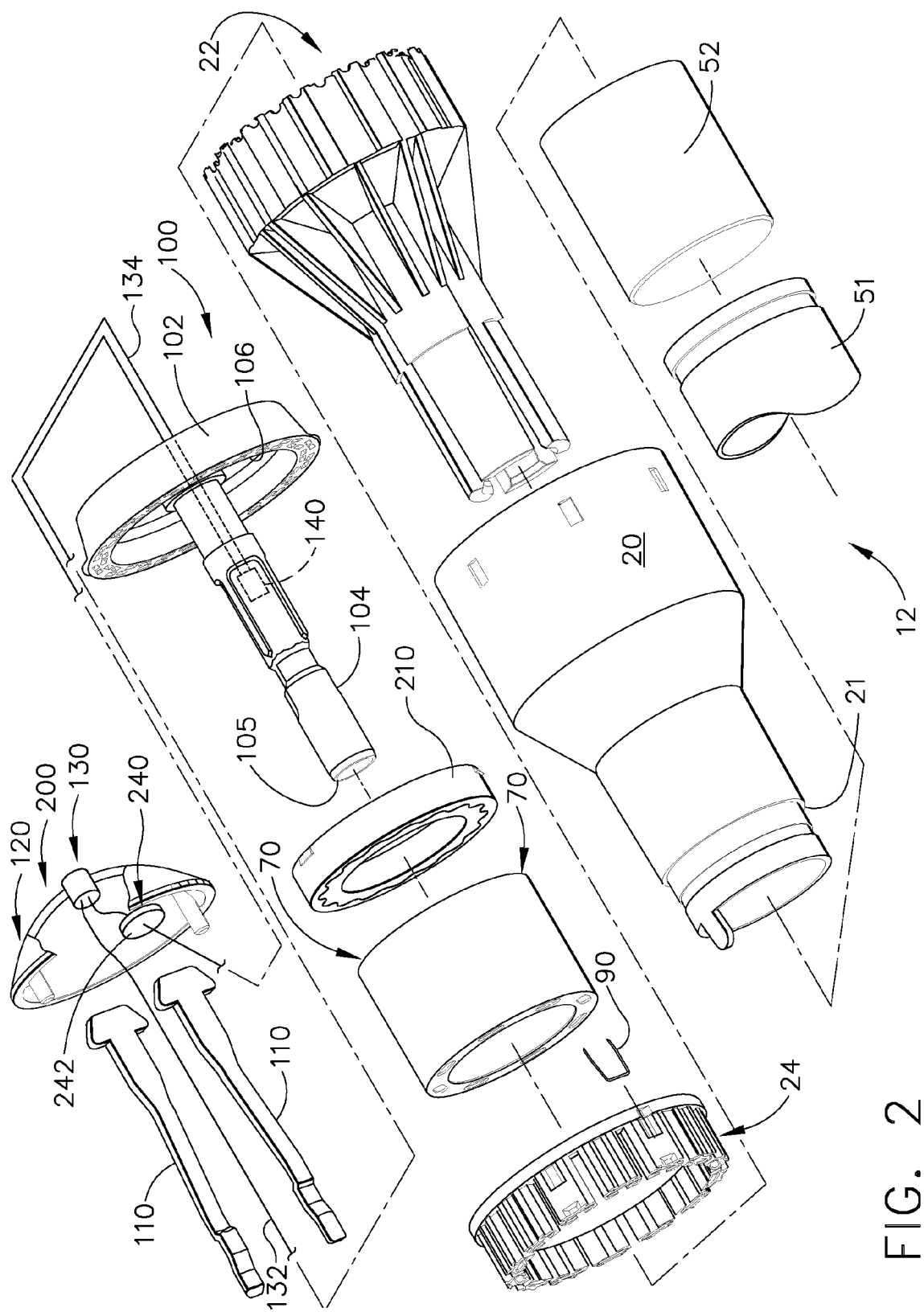
FIG. 2 is an exploded assembly view of the staple head assembly of the surgical stapler depicted in FIG. 1.

FIG. 2 illustrates one form of anvil 100 and stapling head assembly 12 that may be employed in connection with various embodiments of the subject invention. As can be seen in that Figure, the anvil 100 may have a circular body portion 102 that has an anvil shaft 104 for attaching a trocar 60 (FIG. 3) thereto. The anvil body 102 has a staple forming undersurface 106 thereon. In various embodiments, a shroud 120 is attached to the distal end of the anvil body 102. The anvil 100 may be further provided with a pair of trocar retaining clips or leaf-type springs 110 that serve to releasably retain the trocar 60 in retaining engagement with the anvil shaft 104 as will be discussed in further detail below.

As can also be seen in FIG. 2, the stapling head assembly 12 may comprise a casing member 20 that supports a cartridge supporting assembly in the form of a staple driver 22 that is adapted to interface with a circular staple cartridge 24 and drive staples 90 supported therein into forming contact with the staple forming undersurface 106 of anvil 100. A circular knife 70 is centrally disposed within the staple driver 22 and has a distal cutting edge 72 formed thereon. The proximal end 21 of the casing member 20 may be coupled to an outer tubular shroud 51 of the shaft assembly 50 by a distal ferrule member 52.

Figure 3:
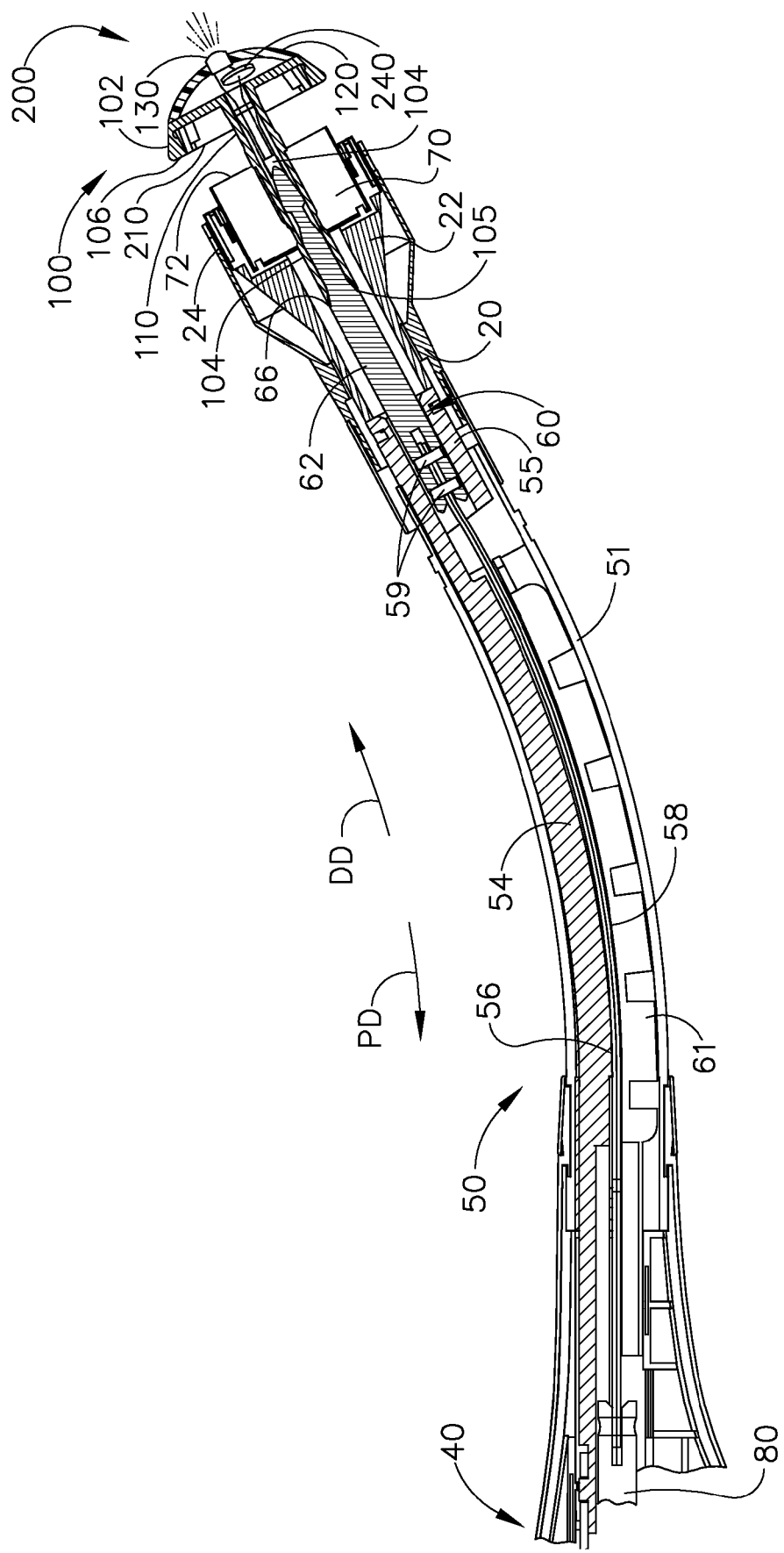
FIG. 3 is a cross-sectional view of the shaft and staple head assembly of the surgical stapler of FIG. 1 with the anvil coupled to the trocar.

FIG. 3 illustrates a shaft assembly 50 that operably supports the trocar 60 and compression shaft 54 for axial movement therein. The compression shaft 54 may be axially and movably supported within the outer tubular shroud 51 and include a distal compression shaft portion 55. As can also be seen in FIG. 3, the distal compression shaft portion 55 is coupled to the staple driver 22. Thus, axial movement of the compression shaft portion 55 within the outer tubular shroud 51 causes the staple driver 22 to move axially within the casing member 20. Actuation of the firing trigger 14 (FIG. 1) will cause the compression shaft 54 and the distal compression shaft portion 55 to move in the distal direction (arrow "DD") thereby driving the staple driver 22 distally to fire the staples 90 into forming contact with the staple forming undersurface 106 of the anvil 100. As the staple driver 22 is driven distally, it also drives the cutting edge 72 of the knife 70 through the tissue held within the circumference of the stapled tissue into a knife board 210 mounted in the anvil 100.

The trocar 60 may include a trocar tip 62 that has attached thereto a top tension band 56 and a bottom tension band 58. The trocar tip 62 may be coupled to the top tension band 56 and bottom tension band 58 by fasteners 59 (e.g., screws, studs, posts, etc.). A spacer band 61 is received within the tubular shroud 51 and serves to slidably support the upper and lower tension bands 56, 58 within the shroud 51. The proximal ends of the top tension band 56 and bottom tension band 58 may be attached to a distal end of an adjustment shaft 80. As illustrated in FIG. 3, the tip 62 of the trocar 60 may be inserted into the anvil shaft 104 of the anvil 100 and retained in engagement by the trocar retaining clips 110.

In various embodiments, the adjustment shaft 80 may be axially movably supported within a handle assembly 40 of the type and construction disclosed in U.S. Patent Publication No. US-2008-0078806-A1 to Todd Philip Omaits, et al., filed Sep. 29, 2006 that is owned by the Assignee of the present application and which is herein incorporated by reference in its entirety. However, other handle and firing system arrangements may be employed without departing from the spirit and scope of the present invention.

Figure 4:
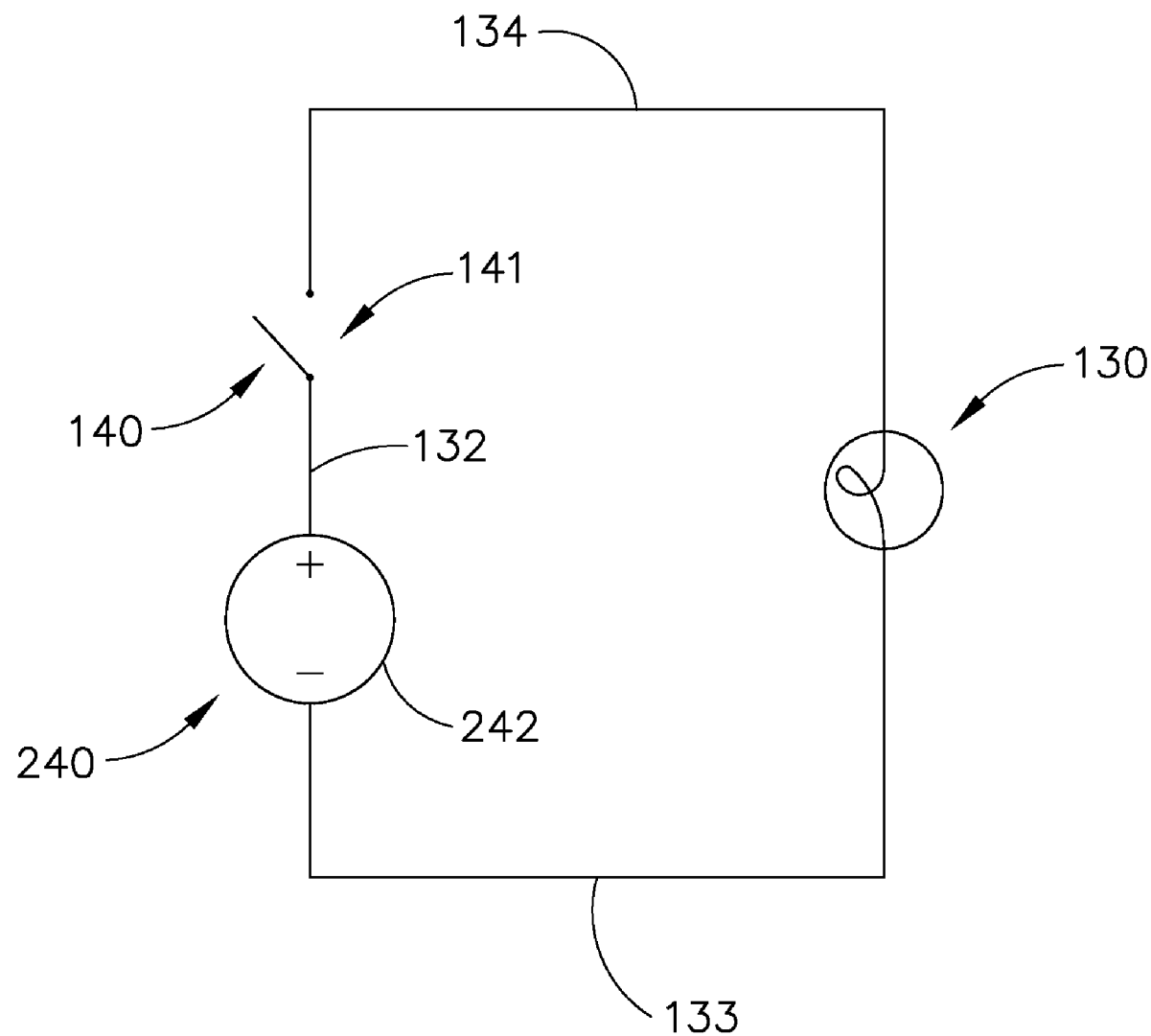
FIG. 4 is a schematic of a control circuit of various embodiments of the present invention.

Various embodiments of the present invention include a unique and novel anvil feedback system generally designated as 200 for, among other things, providing the surgeon with an indication that the anvil 100 has been properly coupled to the trocar 60. One embodiment of the tissue feedback system 200 may include at least one indicator 130 that may be mounted to the distal end of the shroud 120. In various embodiments, for example, the indicator 130 may comprise at least one illumination device such as, for example, at least one light emitting diode (LED) or other lighting device. As can be seen in FIGS. 2 and 4, the indicator 130 may be connected to a Direct Current ("DC") power source 240 that may comprise a battery or number of batteries 242 or other suitable DC power source by a wire or conductor 133. The battery 242 may also be supported within the shroud 120 such that it may be easily installed and replaced. The indicator 130 may also be connected to a sensor 140 that is mounted in the shaft 104 of the anvil 100 by a first wire or conductor 132. The sensor 140 may also be connected to the power source 240 by another conductor or wire 134.

In various embodiments, sensor 140 may comprise a switch 141 that is normally open in its unactuated position such that no current flows to the illumination device light 130 until the switch 141 is closed. The switch 141 is so positioned within or on the shaft 104 of the anvil 100 such that when the trocar tip 62 is properly affixed to the shaft 104 (i.e., seated within the shaft 104 as shown in FIG. 3 and retained in such position by retaining clips 110), the switch 141 is closed which permits the current to flow from the battery 242 to the indicator 130. Switch 141 may comprise a variety of different switch arrangements without departing from the spirit and scope of the present invention. For example, switch 141 may comprise a mechanically actuated switch (i.e., a switch that is mechanically closed by virtue of contact with the trocar tip 62). However, the switch 141 could also be a magnetic switch, etc. that is actuated when the trocar tip 62 has been seated in its properly coupled position within the shaft 104 of the anvil 100.

Those of ordinary skill in the art will appreciate that the anvil feedback system 200 provides an indication to the surgeon that the anvil 100 has been properly coupled to the trocar 60. While only one indicator 130 has been illustrated as being mounted to the shroud 120, it will be understood that more than one indicator could be employed and supported in other orientations on the anvil body 120. Still in other embodiments, one indicator 130 in the form of an illumination device may be supported by the anvil to illuminate the surgical site as well as provide an indication that the anvil has been properly attached and another indicator (not shown) may be supported on the handle assembly or shaft to provide the surgeon with another indication that the anvil has been properly affixed to the trocar 60 without having to specifically look at the anvil or surgical site. Such indicators mounted to the handle assembly could comprise, for example, an illumination device, a sound generating device, a vibration generating device, etc.

Figure 5:
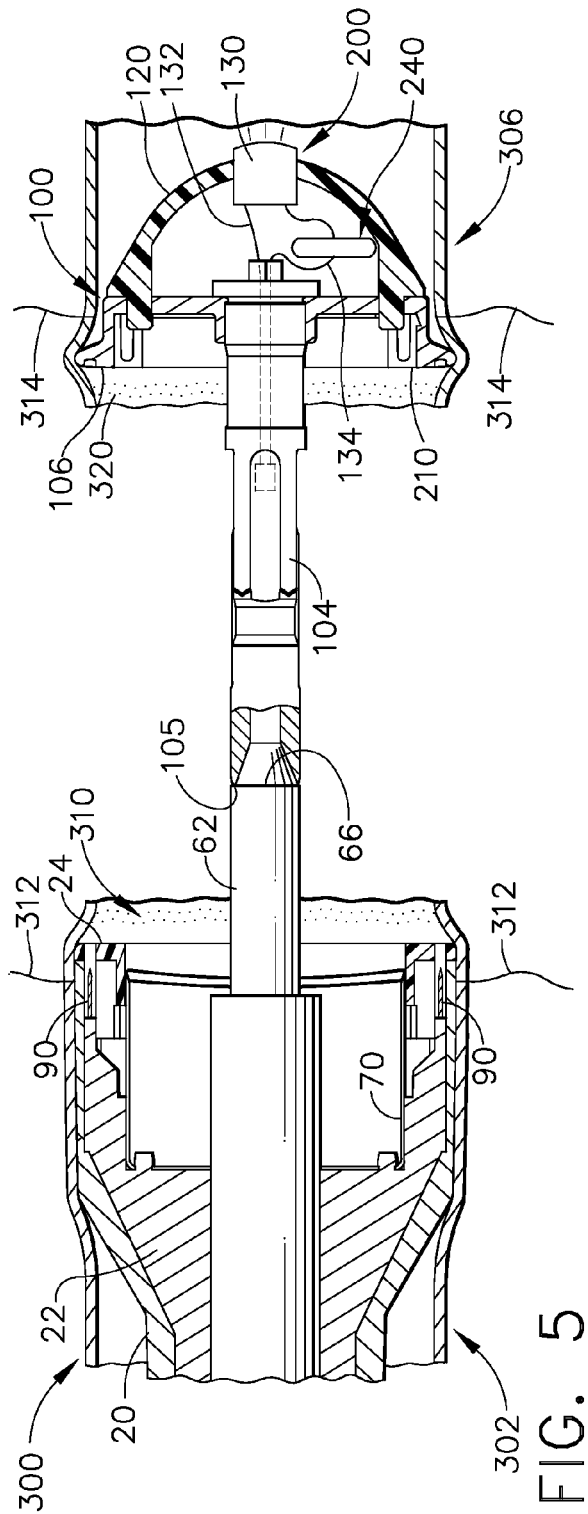
FIG. 5 is a partial cross-sectional view showing the stapler of FIGS. 1-3 in the open position inserted into an intestine after a portion of the intestine has been excised.
Figure 6:
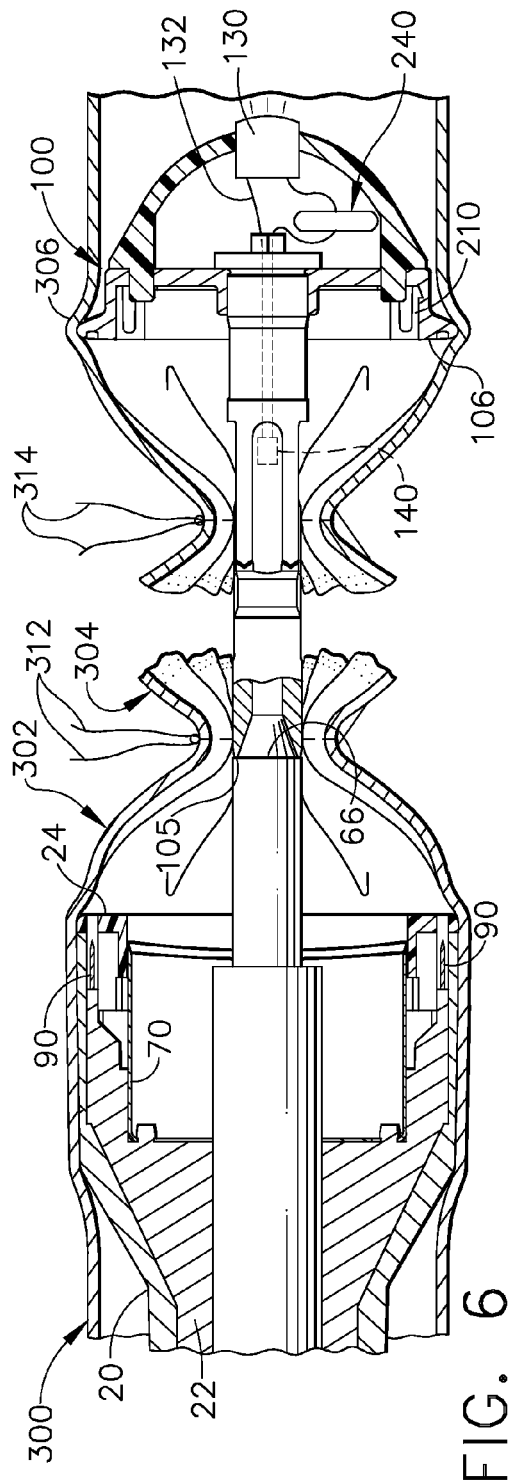
FIG. 6 is another partial cross-sectional view of the stapler of FIG. 5 with the distal end and proximal end of the intestine sewn around the anvil shaft.
Figure 7:
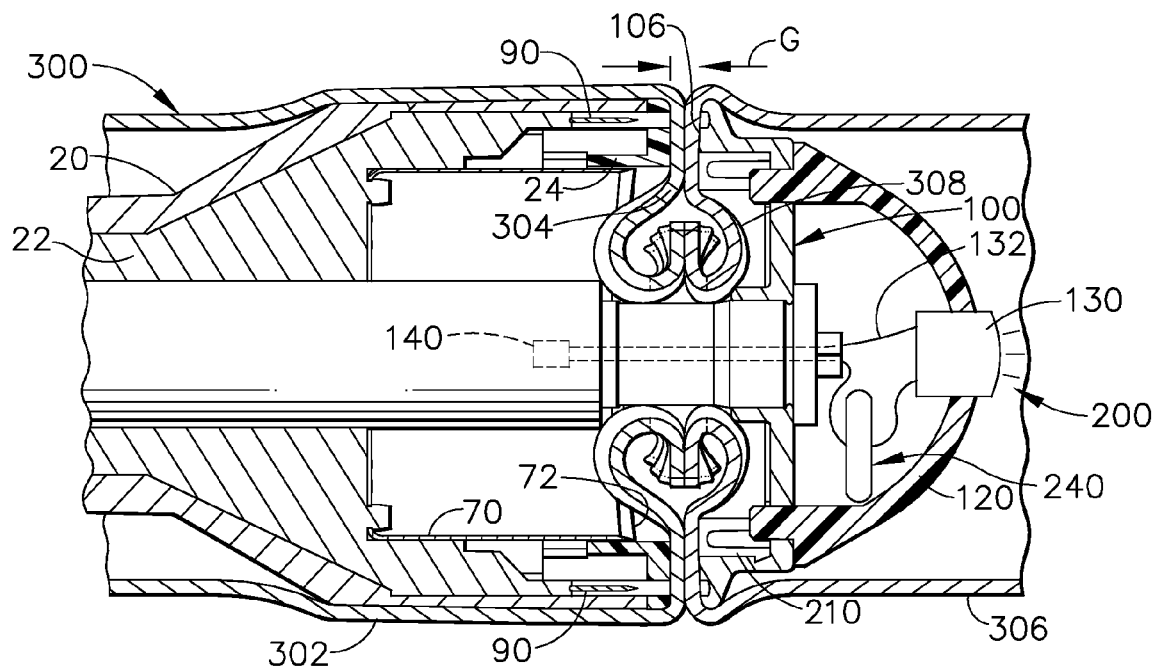
FIG. 7 is another partial cross-sectional view of the stapler of FIGS. 5 and 6 with the anvil drawn into a firing position relative to the stapling head assembly.
Figure 8:
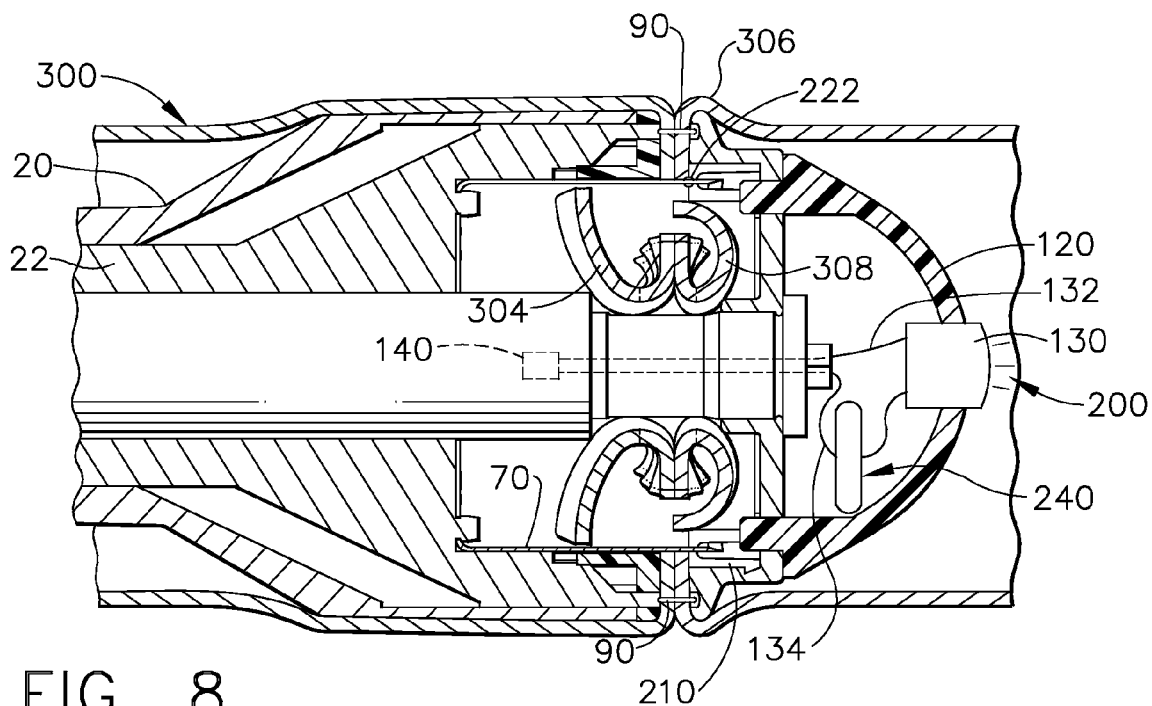
FIG. 8 is another partial cross-sectional view of the stapler of FIGS. 5-7 after it has been fired.

One exemplary method of using the circular stapler 10 will now be described with reference to FIGS. 5-8. When performing an anastomosis using a circular stapler 10, the intestine 300 may be stapled using a conventional surgical stapler with multiple rows of staples being emplaced on either side of a target section (i.e., specimen) of intestine 300. FIG. 5 illustrates the liner staple lines 310, 320. The target section is typically simultaneously cut as the section is stapled. The target section has already been excised in FIG. 5. After removing the target specimen, the surgeon inserts the anvil 100 into the proximal portion 302 of the intestine 300, proximal of the staple line 310. This is done by inserting the anvil head 100 into an entry port cut into the proximal intestine portion 302 or the anvil 100 can be placed transanally, by placing the anvil 100 on the distal end of the stapler 10 and inserting the instrument through the rectum. Next, the surgeon attaches the anvil 100 to the trocar tip 62 of the stapler 100. Once the trocar tip 62 has been inserted into the anvil shaft 104 to a position wherein the proximal end 105 of the anvil shaft 104 is seated on a shoulder portion 66 of the trocar 60 and the retaining clips 110 retainingly engage the trocar tip 62, the switch 140 is closed to permit current to flow from the battery 242 to the indicator 130. The surgeon may observe that the indicator 130 is illuminated by employing a video camera (not shown) that is supported through an endoscope (not shown) to enable the surgeon to view the surgical site (or if another indicator is provided on the handle assembly or shaft assembly, the surgeon may receive an indication from that device that the anvil has been properly attached to the trocar 60). Those of ordinary skill in the art will appreciate that when the indicator 130 comprises at least one illumination device attached to the anvil 100, the indicator 130 provides an indication that the anvil 100 has been properly attached to the trocar 60 as well as illuminates the surgical site.

Once the anvil 100 has been properly coupled to the trocar tip 62, the anvil 100 is inserted into the distal portion 306 of the intestine 300. The surgeon may then tie the distal end 304 of the proximal section 302 of the intestine 300 to the anvil shaft 104 using a suture 312 or other conventional tying device and also tie the proximal end 308 of the distal intestine portion 306 around the anvil shaft using another suture 314. See FIG. 6. The surgeon then begins to rotate the closure knob assembly 30 (FIG. 1) to draw the anvil 100 toward the cartridge 24 supported in the staple driver 22 to close the gap between the anvil 100 and cartridge 24 and thereby engage the proximal end 308 of the distal intestine portion 306 with the distal end 304 of the proximal intestine portion 302 in the gap "G" therebetween. See FIG. 7. The surgeon continues to rotate the closure knob assembly 30 until the desired gap G is attained. When in that "firing" position, the surgeon may then pivot the safety yoke 16 to the off position and fire the stapler 10 by depressing the firing trigger 14. Depressing the trigger 14 causes the compression shaft 54 to drive the staple driver 22 distally to drive the staples 90 to be driven through both ends 304, 308 of the intestine 300, thereby joining the portions 302 and 306 and forming a tubular pathway. Simultaneously, as the staples 908 are driven and formed, the knife 70 is driven through the intestinal tissue ends 304 and 308, cutting the ends adjacent to the inner row of staples 90. See FIG. 8.

Figure 9:
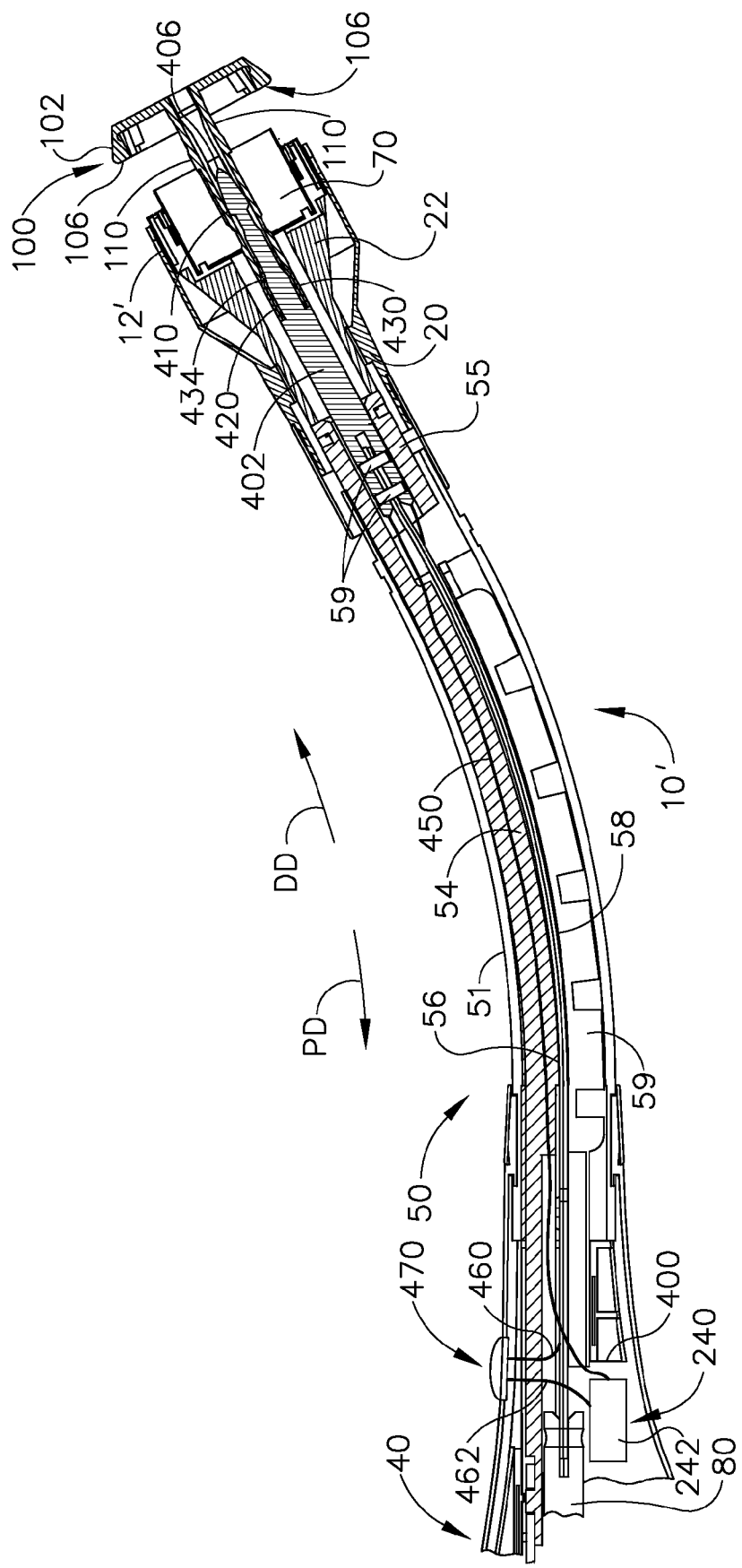
FIG. 9 is a cross-sectional view of the shaft and staple head assembly of another surgical stapler embodiment of the present invention with the anvil coupled to the trocar.

FIGS. 9-11 illustrate another circular stapler 10' that may employ some unique and novel features of the present invention. Those components of stapler 10' that are identical to the above-described components are labeled with like numbers. In one embodiment, for example, the anvil 100 lacks the indicator 130 of the prior embodiments. In this embodiment, however, the trocar 400 is formed with two or more contact regions 410 and 434 that are electrically isolated from each other by an electrical insulator 420. More specifically and with reference to FIGS. 10 and 11, the trocar 400 includes a body portion 402 that is coupled to the top tension band 56 and bottom tension band 58 by fasteners 59 in the manner described above. The body portion 402 has a distal end portion 404 that terminates in tip 406 and which has the first contact region or shoulder 410 formed thereon. The body 402 of the trocar 400 is fabricated from an electrically conductive material such as, for example, stainless steel, titanium, aluminum, etc. Received on distal portion 404 of the trocar 400 is an electrical insulator sleeve 420 that may be fabricated from, for example, a thermoplastic material such as Vectra®, high density polyethylene (HDPE), Ultem®, etc. Mounted on the electrical insulator 420 is a contact bushing 430. Contact bushing 430 is fabricated from electrically conductive material such as, for example, stainless steel, titanium, aluminum, etc. The contact bushing 430 has a distal shoulder 432 formed thereon which defines a second contact surface 434 for engagement with the proximal end portion 105 of the hollow anvil shaft 104.

A first conductor or wire 450 is connected to the contact bushing 430. In various embodiments, the contact bushing 430 may have a slot or groove 438 sized to receive an end of the conductor 450 which may be soldered, and/or glued or otherwise electrically connected thereto. A second conductor or wire 460 maybe attached to body portion 402 by one or both of the fasteners 59 that also serve to couple the top and bottom tension bands 56, 58 thereto. However, the second conductor 450 may be electrically coupled to the body portion 402 of the trocar 400 by other suitable methods.

Figure 12:
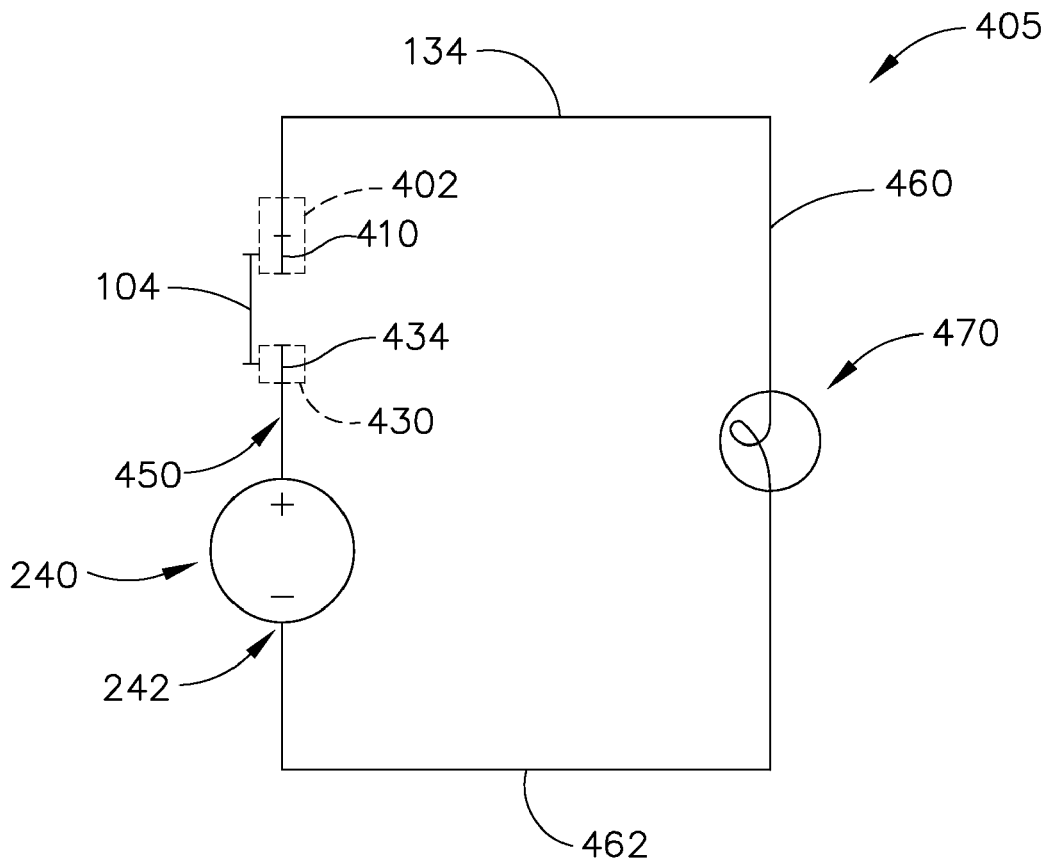
FIG. 12 is a schematic view of a control circuit of other embodiments of the present invention.
Figure 13:
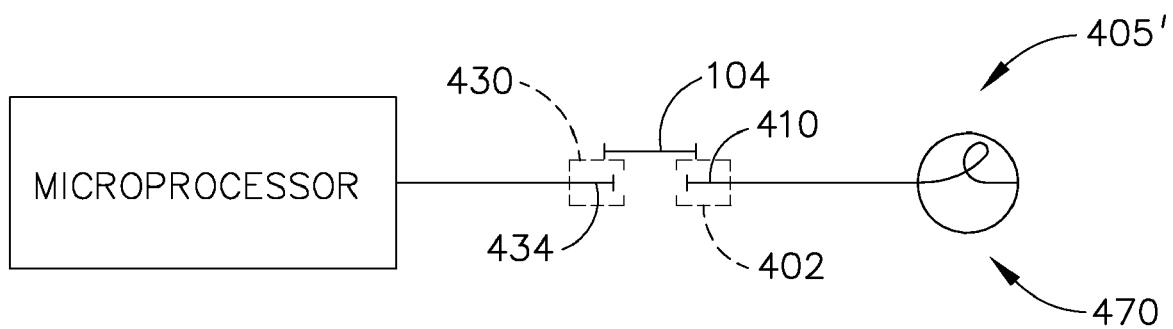
FIG. 13 is a schematic view of another control circuit arrangement of other embodiments of the present invention.

FIG. 12 depicts one form of an indicator circuit 405 that may be employed. As can be seen in that Figure, a Direct Current ("DC") power source 240, that may comprise a battery or number of batteries 242 or other suitable DC power source, is connected to the contact bushing 430 which is mounted on the electrical insulator 420 that is mounted on the trocar body 402 as illustrated in FIGS. 10 and 11. The second conductor 460 is connected to the electrically conductive trocar body 402 and an indicator 470 that is mounted on the handle assembly 40. The indicator 470 is, in turn, connected to the power source 240 by a conductor 462. The indicator 470 may comprise at least one light emitting diode ("LED") or other suitable light source. Thus, when the shaft 104 of the anvil 100 is properly received on the distal portion 404 such that the proximal end 104 of the shaft 104 is seated on the second contact region 434, the shaft 104 is also in contact with the first contact region 410 which completes the circuit 405 and cause the indicator 470 to be energized. See FIG. 11. Such arrangement provides the surgeon with a positive indication that the anvil 100 has been properly attached to the trocar 400. FIG. 13 illustrates an alternative indicator circuit 405' which employs a microprocessor 480 that may be housed within the handle assembly 40 to control the indicator 470 when the anvil 100 has been attached to the trocar 400 to complete the circuit.

As was discussed above, once the anvil 100 has been properly coupled to the trocar 400, the anvil 100 is inserted into the distal portion 306 of the intestine 300. The surgeon may then tie the distal end 304 of the proximal section 302 of the intestine 300 to the anvil shaft 104 using a suture 312 or other conventional tying device and also tie the proximal end 308 of the distal intestine portion 306 around the anvil shaft using another suture 314. The surgeon then begins to rotate the closure knob assembly 30 (FIG. 1) to draw the anvil 100 toward the cartridge 24 supported in the staple driver 22 to close the gap between the anvil 100 and cartridge 24 and thereby engage the proximal end 308 of the distal intestine portion 306 with the distal end 304 of the proximal intestine portion 302 in the gap "G" therebetween. The surgeon continues to rotate the closure knob assembly 30 until the desired gap G is attained. To assist the surgeon in determining when the anvil 100 has been moved to the desired firing position relative to the staple cartridge 24, various embodiments may also be provided with a closure circuit 500.

Figure 14:
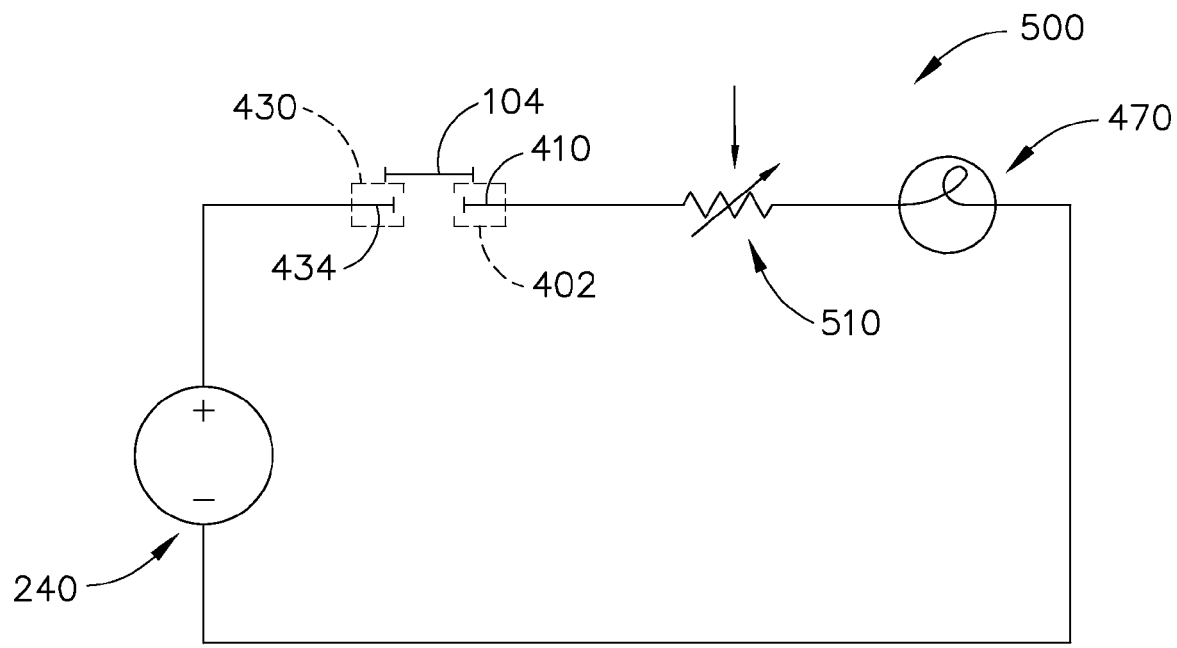
FIG. 14 is a schematic view of another control circuit arrangement of other embodiments of the present invention.

More particularly and with reference to FIG. 14, the closure circuit 500 may include the power source 240, the first contact region 410 on the body portion 402 of the trocar 400 and a second contact region 434 formed on the contact bushing 430 as was described above as well as a string potentiometer 510 or other distance sensor to control a variable resistor. The string potentiometer 510 is configured and mounted within the shaft 50 or handle assembly 40 and coupled to the trocar 400 or adjustment shaft 80 to detect the axial distance that the trocar 400 moves in the proximal "PD" direction from a starting position wherein the anvil 100 has been properly coupled thereto. When employing this feature, the trocar 400 may be positioned (by virtue of rotating the control knob 30) in a starting position wherein the anvil 100 may be attached thereto in the manner described above. The string potentiometer 510 is set such that resistance is low when the anvil 100 has been properly coupled to the trocar 400 in the starting position. Thus, when the anvil 100 has been attached to the trocar 400, resistance is low and the indicator 470 is energized to provide the surgeon with an indication that the anvil 100 has been properly attached. As the surgeon then rotates the adjustment knob 30 to draw the anvil 100 proximally toward the cartridge 24, resistance in the string potentiometer 510 increases and reduces the amount of current flowing to the indicator 270 thereby dimming the indicator 270 until the anvil reaches a desired firing position (i.e., the desired gap "G" has been achieved). At that point, the resistance is increased to a level wherein little or no current flows to the indicator light 270 to cause it to go out. Thus, the surgeon can watch the indicator 270 during the closing process and when the light goes out, the surgeon knows that the anvil 100 has been positioned in the desired firing position.

Figure 15:
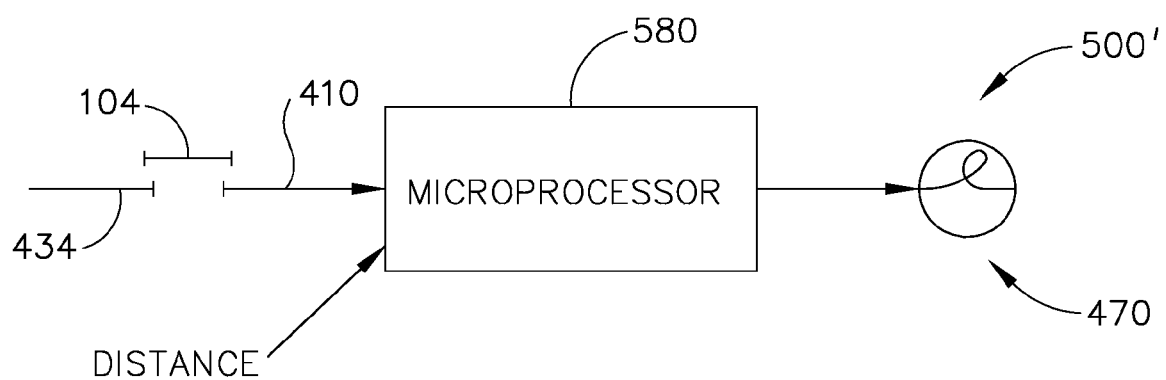
FIG. 15 is a schematic view of a control circuit of other embodiments of the present invention.

While this embodiment employs a string potentiometer to adjust the resistance in the closure circuit 500 as the trocar 400 and anvil 100 are adjusted, other circuit arrangements may be employed. For example, a transistor based amplifier such as a Darlington pair that is controlled by the axial distance that the trocar 400 is moved may be employed. In still other embodiments, a circuit 500' may be employed which includes a microprocessor 580 for controlling the illumination of the indicator 270 as the anvil 100 is axially advanced to a desired closed position. See FIG. 15.

The various embodiments of the present invention represent a vast improvement over prior circular staple arrangements that fail to provide any means of indicating when the anvil has been properly attached to the trocar and/or also providing an indication of when the anvil has been positioned in an orientation relative to the staple cartridge that is ready for firing. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical stapling instrument for applying one or more surgical staples tissue, comprising:
  a handle assembly;
  a shaft assembly coupled to said handle assembly and movably supporting a trocar assembly therein;
  a stapling head assembly operably coupled to said shaft assembly, said stapling head assembly comprising:
    a staple cartridge for supporting one or more surgical staples;
    a staple driver for engaging and driving the staples from said staple cartridge; and
    a knife movable supported in said stapling head assembly;
  a drive system for applying drive motions to said staple driver and said knife;
  an anvil removably attachable to a distal end of said trocar assembly; and
  an anvil feedback system operably communicating with said trocar assembly for providing an indication signal when said anvil is attached to said distal end of said trocar assembly, said anvil feedback system comprising at least one sensor on one of said distal end of said trocar assembly and said anvil, said at least one sensor communicating with an indicator on said surgical stapling instrument to provide an indication signal thereto.

2. The surgical stapling instrument of claim 1 wherein said indicator is on said anvil.

3. The surgical stapling instrument of claim 2 wherein said indicator comprises at least one illumination device.

4. The surgical stapling instrument of claim 3 wherein said at least on illumination device comprises at least one light emitting diode.

5. The surgical stapling instrument of claim 2 further comprising a power source supported on said anvil and coupled to said indicator and said at least one sensor.

6. The surgical stapling instrument of claim 1 wherein said anvil feedback system comprises:
   an indicator supported on one of said handle assembly, shaft assembly or anvil; and
   a source of electrical current connected to said trocar assembly and said indicator such that electrical current only flow to said indicator from said source of electrical current when said anvil is attached to said distal end of said trocar assembly.

7. The surgical stapling instrument of claim 6, wherein said indicator comprises an indicator selected from the group of indicators consisting of: a light generating device, a vibration generating device, and a sound generating device.

8. The surgical stapling instrument of claim 6 wherein said trocar assembly has a plurality of contact regions thereon that communicate with said source of electrical current and said indicator, at least one of said contact regions electrically insulated from at least one other said contact regions such that when said anvil is not attached to said distal end of said trocar assembly, no electrical current flows from said source of electrical current to said indicator and when said anvil is attached to said distal end of said trocar assembly, said anvil electrically connects said electrically insulated contact regions to permit said electrical current to flow to said indicator.

9. The surgical stapling instrument of claim 1 further comprising an actuating mechanism operably supported on said handle assembly and coupled to said trocar assembly for selectively actuating said trocar assembly within said shaft assembly such that when said anvil is attached to said distal end portion of said trocar assembly, said actuating mechanism may move said trocar assembly to position said anvil at a desired firing position relative to said staple cartridge and wherein said anvil feedback system is further configure to indicate when said anvil has been positioned in said desired firing position.

10. The surgical stapling instrument of claim 9 wherein said anvil feedback system discontinues said indication signal when said anvil has been positioned in said desired firing position.

11. A surgical stapling instrument for applying one or more surgical staples to tissue, comprising:
   a handle assembly;
   a shaft assembly coupled to said handle assembly and movably supporting a trocar assembly therein;
   a stapling head assembly operably coupled to said shaft assembly, said stapling head assembly comprising:
      a staple cartridge for supporting one or more surgical staples;
      a staple driver for engaging and driving the staples from said staple cartridge; and
      a knife movably supported in said stapling head assembly;
   a drive system for applying drive motions to said staple driver and said knife;
   an anvil removably attachable to a distal end of said trocar assembly;
   an illumination device attached to said anvil, said illumination device electrically connected to a source of electrical current; and
   at least one sensor on one of said anvil and said trocar assembly and electrically coupled to said source of electrical current and said illumination device such that when said anvil is attached to said distal end portion of said trocar assembly, electrical current flows from said source of electrical current to said illumination device.

12. The surgical stapling instrument of claim 11 wherein said illumination device comprises at least one light emitting diode.

13. The surgical stapling instrument of claim 11 further comprising a shroud attached to distal end of said anvil and wherein illumination device is attached to said shroud.

14. The surgical stapling instrument of claim 11 wherein said source of electrical current comprises at least one battery supported by said surgical instrument.

15. A surgical stapling instrument for applying one or more surgical staples to tissue, comprising:
   a handle assembly;
   a shaft assembly coupled to said handle assembly;
   a stapling head assembly operably coupled to said shaft assembly, said stapling head assembly comprising:
      a stapling cartridge for supporting one or more surgical staples;
      a staple driver for engaging and driving the staples from said staple cartridge; and
      a knife movably supported in said stapling head assembly;
   a drive system for applying drive motions to said staple driver and said knife;
   a source of electrical current;
   a indicator on said instrument, said indicator communicating with said source of electrical current; and
   a trocar assembly movably supported by said shaft assembly configured to detachably support an anvil thereon, said trocar assembly having a first contact region and a second contact region that communicate with said source of electrical current and said indicator, said second contact region being electrically insulated from said first contact region such that when said anvil is attached to said distal end of said trocar assembly, said anvil electrically connects said first and second contact regions to permit said electrical current flow to said indicator.

16. The surgical instrument of claim 15 further comprising:
   an actuating mechanism operably supported on said handle assembly and coupled to said trocar assembly for selectively actuating said trocar assembly within said shaft assembly such that when said anvil is attached to said distal end portion of said trocar assembly, said adjustment mechanism may move said trocar assembly to locate said anvil at a desired firing position relative to said staple cartridge; and
   means communicating with said trocar assembly and said source of electrical current to limit the flow of electrical current from said source of electrical current to said indicator as said trocar assembly moves said anvil towards said staple cartridge.

17. The surgical instrument of claim 16 wherein said means communicating with said trocar assembly prevents the flow of electrical current to said indicator when said anvil has been positioned in said desired firing position.

18. The surgical stapling instrument of claim 15, wherein said indicator comprises an indicator selected from the group of indicators consisting of: a light emitting device, a vibration generating device, and a sound generating device.

19. The surgical stapling instrument of claim 15 wherein said indicator comprises at least one light emitting device supported on said handle assembly.

* * * * *